(12) United States Patent
Liu et al.

(10) Patent No.: US 7,598,380 B2
(45) Date of Patent: Oct. 6, 2009

(54) METHOD OF PREPARATION OF AZAINDOLE DERIVATIVES

(75) Inventors: Wansheng Liu, Edison, NJ (US); Sunil S. Patel, Edison, NJ (US); Nicolas Cuniere, Belle Mead, NJ (US); Yvonne Lear, Candiac (CA); Prashant P. Deshpande, Princeton, NJ (US); Jeffrey N. Simon, Lawrenceville, NJ (US); Chiajen Lai, Kendall Park, NJ (US); Annie J. Pullockaran, Pennington, NJ (US); Nachimuthu Soundararajan, Kendall Park, NJ (US); Jeffrey T. Bien, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 265 days.

(21) Appl. No.: 11/492,750

(22) Filed: Jul. 25, 2006

(65) Prior Publication Data
US 2007/0032503 A1 Feb. 8, 2007

Related U.S. Application Data

(60) Provisional application No. 60/705,230, filed on Aug. 3, 2005.

(51) Int. Cl.
C07D 487/04 (2006.01)
C07D 213/69 (2006.01)
C07D 213/73 (2006.01)
(52) U.S. Cl. .................. 544/362; 546/296; 546/311
(58) Field of Classification Search .............. None
See application file for complete search history.

(56) References Cited

U.S. PATENT DOCUMENTS

| | | | |
|---|---|---|---|
| 3,135,794 A | 6/1964 | Archer | |
| 4,791,104 A | 12/1988 | Picciola et al. | |
| 5,023,265 A | 6/1991 | Scherlock et al. | |
| 5,124,327 A | 6/1992 | Greenlee et al. | |
| 5,192,770 A | 3/1993 | Clark et al. | |
| 5,413,999 A | 5/1995 | Vacca et al. | |
| 5,424,329 A | 6/1995 | Boschelli et al. | |
| 5,811,432 A | 9/1998 | Marfat et al. | |
| 6,008,231 A | 12/1999 | Lebaut et al. | |
| 6,172,085 B1 | 1/2001 | Ohkawa et al. | |
| 6,232,327 B1 | 5/2001 | Nickel et al. | |
| 6,469,006 B1 | 10/2002 | Blair et al. | |
| 6,476,034 B2 | 11/2002 | Wang et al. | |
| 6,573,262 B2 | 6/2003 | Wallace et al. | |
| 6,632,819 B1 | 10/2003 | Wang et al. | |
| 6,825,201 B2 | 11/2004 | Wang et al. | |
| 6,900,206 B2 | 5/2005 | Kadow et al. | |
| 6,900,323 B2 | 5/2005 | Wang et al. | |
| 7,037,913 B2 | 5/2006 | Wang et al. | |
| 7,087,610 B2 | 8/2006 | Wang et al. | |
| 2003/0207910 A1* | 11/2003 | Wang et al. | 514/300 |
| 2005/0148636 A1* | 7/2005 | Carson et al. | 514/343 |
| 2006/0293304 A1* | 12/2006 | Soundararajan et al. | 514/210.21 |

FOREIGN PATENT DOCUMENTS

| | | |
|---|---|---|
| WO | WO 01/62255 | 8/2001 |
| WO | WO 03/072028 | 9/2003 |

* cited by examiner

*Primary Examiner*—Emily Bernhardt
(74) *Attorney, Agent, or Firm*—John F. Levis; Jennifer Chin Chapman

(57) ABSTRACT

A method of preparing azaindole compounds for antiviral use having the formula

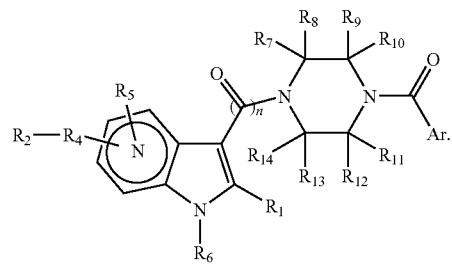

15 Claims, No Drawings

METHOD OF PREPARATION OF AZAINDOLE DERIVATIVES

CROSS-REFERENCE TO RELATED APPLICATIONS

This application claims the benefit of U.S. Provisional Application Ser. No. 60/705,230 filed Aug. 3, 2005.

FIELD OF THE INVENTION

The present invention provides a method of preparing an azaindole derivative. The azaindole derivative demonstrates antiviral activity for treatment of HIV and AIDS.

BACKGROUND OF THE RELATED TECHNOLOGY

HIV-1 (human immunodeficiency virus-1) infection remains a major medical problem, with an estimated 33.6 million people infected worldwide. The number of cases of HIV and AIDS (acquired immunodeficiency syndrome) has risen rapidly. In 1999, 5.6 million new infections were reported, and 2.6 million people died from AIDS. Currently available drugs for the treatment of HIV include six nucleoside reverse transcriptase (RT) inhibitors (zidovudine, didanosine, stavudine, lamivudine, zalcitabine and abacavir), three non-nucleoside reverse transcriptase inhibitors (nevirapine, delavirdine and efavirenz), and five peptidomimetic protease inhibitors (saquinavir, indinavir, ritonavir, nelfmavir and amprenavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vaccaand Condra; Flexner; Berkhout and Ren et al; (Ref 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in thetherapy of HIV infections (Pedersen & Pedersen, Ref. 15). At least 30 different classes of NNRTI have been described in the literature (De Clercq, Ref. 16) and several NNRTIs have been evaluated in clinical trials. Dipyridodiazepinone (nevirapine), benzoxazinone (efavirenz) and bis(heteroaryl)piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen &Pedersen, Ref. 15).

Certain azaindole derivatives have demonstrated inhibitory activity against HIV. Such compounds, include the compound of formula 8:

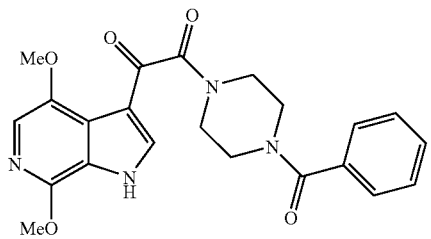

8 which is disclosed in U.S. Pat. No. 6,476,034, herein incorporated by reference in its entirety.

In order to promote the development and production of effective new drugs and treatments for HIV, such as the compounds of U.S. Pat. No. 6,476,034, new methods of preparing these drugs which are more cost and time efficient are required. The present invention seeks to provide such methods.

SUMMARY OF THE INVENTION

One aspect of the present invention provides a method of preparing compounds of formula 25:

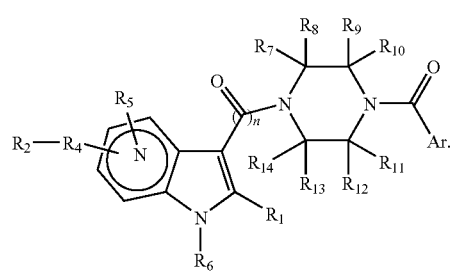

25

The method of preparing the compound of formula 25 includes the steps of:
(a) converting a compound of formula 20:

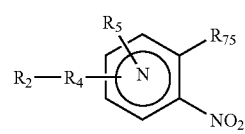

20 to a compound of formula 22:

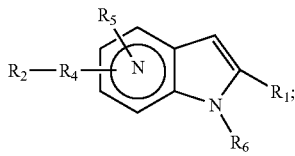

22

(b) converting the compound of formula 22 to a compound of formula 23:

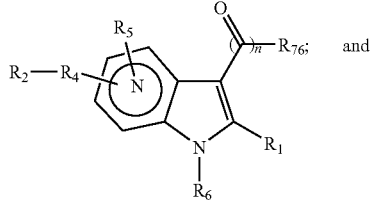

(c) coupling the compound of formula 23 with a compound of formula 24:

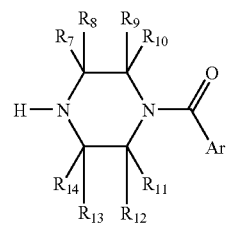

Another aspect of the present invention provides a method of preparing a compound of formula 8:

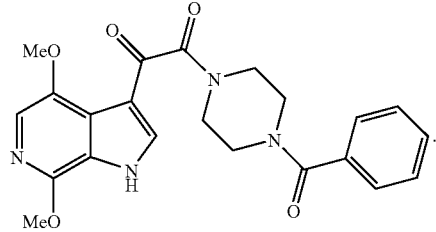

Other aspects of the invention, including methods of preparing useful intermediates, are also provided in each step below. The method of preparing the compound of formula 8 includes the steps of:

(a) converting a compound of formula 1:

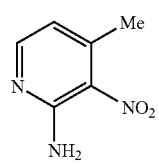

to a compound of formula 2:

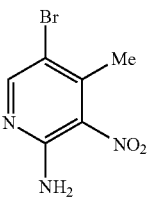

(b) converting said compound of formula 2 to a compound of formula 3:

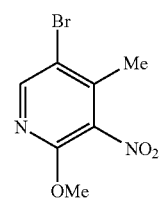

(c) converting said compound of formula 3 to a compound of formula 4:

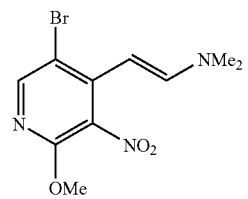

(d) converting said compound of formula 4 to a compound of formula 5:

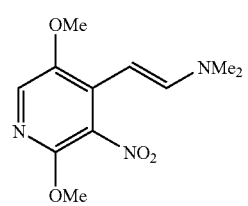

(e) cyclizing said compound of formula 5 to a compound of formula 6:

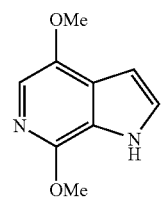

(f) converting said compound of formula 6 to a compound of formula 7:

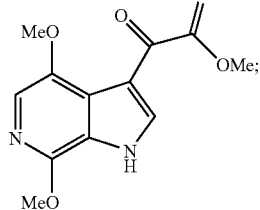

and (g) coupling said compound of formula 7 with a compound of formula 9:

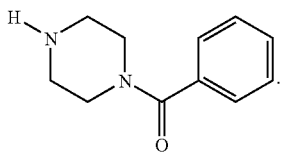

Another aspect of the present invention provides a method of isolating and crystallizing the compound of formula 8 from the reaction mixture that results from step (g). This method includes the introduction of N-methylpyrrolidone (NMP) and water to the mixture including the compound of formula 8. After the compound of formula 8 is isolated, it may then be recrystallized using an isopropyl alcohol/water recrystallization solvent.

DETAILED DESCRIPTION OF THE INVENTION

The present invention relates to a method of preparing compounds of formula 25:

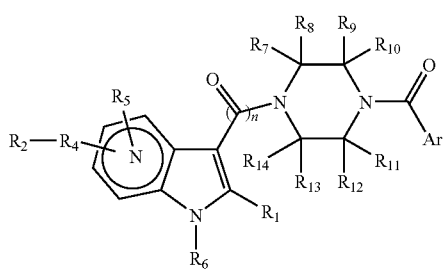

wherein,

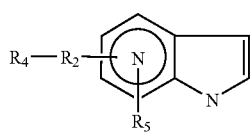

is selected from the group consisting of

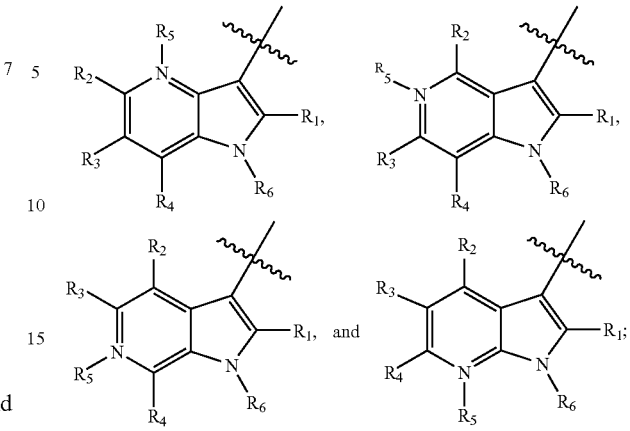

$R_1$, $R_2$, $R_3$, $R_4$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, halogen, CN, phenyl, nitro, $C(O)R_{15}$, $C(O)OR_{16}$, $C(O)NR_{17}R_{18}$, $OR_{19}$, $SR_{20}$ and $NR_{21}R_{22}$;

$R_{15}$, is independently selected from the group consisting of H, $C_1$-$C_6$ alkyl, $C_3$-$C_6$ cycloalkyl, $C_2$-$C_6$ alkenyl, and $C_4$-$C_6$ cycloalkenyl;

$R_{16}$, $R_{19}$, and $R_{20}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl provided the carbons which comprise the carbon-carbon triple bond of said $C_3$-$C_6$ alkynyl are not the point of attachment to the oxygen or sulfur to which $R_{16}$, $R_{19}$, or $R_{20}$ is attached;

$R_{17}$ and $R_{18}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl provided the carbons which comprise the carbon-carbon double bond of said $C_3$-$C_6$ alkenyl or the carbon-carbon triple bond of said $C_3$-$C_6$ alkynyl are not the point of attachment to the nitrogen to which $R_{17}$ and $R_{18}$ is attached;

$R_{21}$ and $R_{22}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl and $C(O)R_{23}$ provided the carbons which comprise the carbon-carbon double bond of said $C_3$-$C_6$ alkenyl, $C_4$-$C_6$ cycloalkenyl, or the carbon-carbon triple bond of said $C_3$-$C_6$ alkynyl are not the point of attachment to the nitrogen to which $R_{21}$ and $R_{22}$ is attached;

$R_{23}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

$R_5$ is $(O)_m$, wherein m is 0 or 1;

n is 1 or 2;

$R_6$ is selected from the group consisting of H, $C_1$-$C_6$ alkyl, $C_3$-$C_6$ cycloalkyl, $C_4$-$C_6$ cycloalkenyl, $C(O)R_{24}$, $C(O)OR_{25}$, $C(O)NR_{26}R_{27}$, $C_3$-$C_6$ alkenyl and $C_3$-$C_6$ alkynyl, provided the carbons which comprise the carbon-carbon double bond of said $C_3$-$C_6$ alkenyl or the carbon-carbon triple bond of said $C_3$-$C_6$ alkynyl are not the point of attachment to the nitrogen to which $R_6$ is attached;

$R_{24}$ is selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl;

$R_{25}$ is selected from the group consisting of $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl, provided the carbons which comprise the carbon-carbon triple bond of said $C_3$-$C_6$alkynyl are not the point of attachment to the oxygen to which $R_{25}$ is attached;

$R_{26}$ and $R_{27}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, and $C_3$-$C_6$ alkynyl provided the carbons which comprise the carbon-carbon double bond of said $C_3$-$C_6$ alkenyl, $C_5$-$C_6$ cycloalkenyl, or the carbon-carbon triple bond of said $C_3$-$C_6$ alkynyl are not the point of attachment to the nitrogen to which $R_{26}$ and $R_{27}$ are attached;

$R_7$, $R_8$, $R_9$, $R_{10}$, $R_{11}$, $R_{12}$, $R_{13}$, and $R_{14}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, $CR_{28}R_{29}OR_{30}$, $C(O)R_{31}$, $CR_{32}(OR_{33})OR_{34}$, $CR_{35}NR_{36}R_{37}$, $C(O)OR_{38}$, $C(O)NR_{39}R_{40}$, $CR_{41}R_{42}F$, $CR_{43}F_2$ and $CF_3$;

$R_{28}$, $R_{29}$, $R_{30}$, $R_{31}$, $R_{32}$, $R_{35}$, $R_{41}$, $R_{42}$ and $R_{43}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl and $C(O)R_{44}$;

$R_{33}$, $R_{34}$ and $R_{38}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl, provided the carbons which comprise the carbon-carbon triple bond of said $C_3$-$C_6$ alkynyl are not the point of attachment to the oxygen to which $R_{34}$ and $R_{38}$ are attached;

$R_{36}$ and $R_{37}$ are each independently selected from the group consisting of H, $C_1$-$C_6$ alkyl, $C_3$-$C_6$ cycloalkyl, $C_3$-$C_6$ alkenyl, $C_4$-$C_6$ cycloalkenyl, and $C_3$-$C_6$ alkynyl, provided the carbons which comprise the carbon-carbon triple bond of said $C_3$-$C_6$ alkynyl are not the point of attachment to the nitrogen to which $R_{36}$ and $R_{37}$ are attached;

$R_{39}$ and $R_{40}$ are each independently selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_3$-$C_6$ alkynyl, provided the carbons which comprise the carbon-carbon triple bond of said $C_3$-$C_6$ alkynyl are not the point of attachment to the nitrogen to which $R_{39}$ and $R_{40}$ are attached;

$R_{44}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, and $C_2$-$C_6$ alkynyl;

Ar is selected from the group consisting of

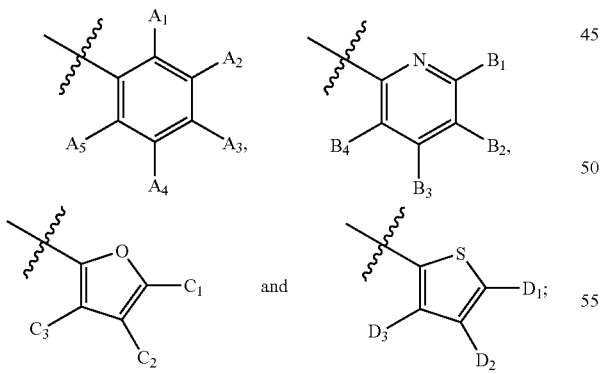

$A_1$, $A_2$, $A_3$, $A_4$, $A_5$, $B_1$, $B_2$, $B_3$, $B_4$, $C_1$, $C_2$, $C_3$, $D_1$, $D_2$, and $D_3$ are each independently selected from the group consisting of H, CN, halogen, $NO_2$, $C_1$-$C_6$ alkyl, $C_3$-$C_6$ cycloalkyl, $C_2$-$C_6$ alkenyl, $C_4$-$C_6$ cycloalkenyl, $C_2$-$C_6$ alkynyl, $OR_{45}$, $NR_{46}R_{47}$, $S_{48}$, $N_3$ and CH(—N=N—)—$CF_3$;

$R_{45}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl and $C_3$-$C_6$ alkynyl, provided the carbons which comprise the car-bon-carbon triple bond of said $C_3$-$C_6$ alkynyl are not the point of attachment to the oxygen to which $R_{45}$ is attached;

$R_{46}$ and $R_{47}$ are each independently selected from the group consisting of H, $C_1$-$C_6$ alkyl, $C_3$-$C_6$ cycloalkyl, $C_3$-$C_6$ alkenyl, $C_5$-$C_6$ cycloalkenyl, $C_3$-$C_6$ alkynyl and $C(O)R_{50}$, provided the carbons which comprise the carbon-carbon double bond of said $C_5$-$C_6$ alkenyl, $C_4$-$C_6$ cycloalkenyl, or the carbon-carbon triple bond of said $C_3$-$C_6$ alkynyl are not the point of attachment to the nitrogen to which $R_{46}$ and $R_{47}$ are attached;

$R_{48}$ is selected from the group consisting of H, $C_1$-$C_6$ alkyl, $C_3$-$C_6$ cycloalkyl, $C_2$-$C_6$ alkenyl, $C_4$-$C_6$ cycloalkenyl, $C_3$-$C_6$ alkynyl and $C(O)R_{49}$, provided the carbons which comprise the carbon-carbon triple bond of said $C_3$-$C_6$ alkynyl are not the point of attachment to the sulfur to which $R_{48}$ is attached;

$R_{49}$ is $C_1$-$C_6$ alkyl or $C_3$-$C_6$ cycloalkyl;

$R_{50}$ is selected from the group consisting of H, $C_1$-$C_6$ alkyl, and $C_3$-$C_6$ cycloalkyl.

$R_{75}$ is selected from the group consisting of H and $CH_3$; and $R_{76}$ is selected from the group consisting of $C_1$-$C_3$ alkoxy and halogen.

Examples of similar compounds are set forth in commonly assigned Patent Application No. WO 01/62255 and U.S. Pat. No. 6,476,034, the disclosure of each being incorporated herein in its entirety.

One aspect of the present invention is shown below in Scheme 1.

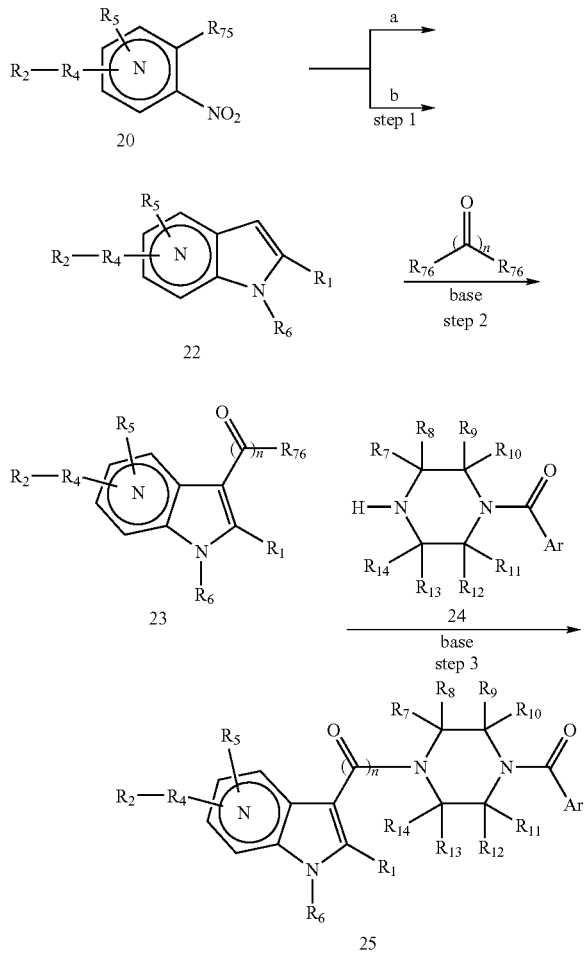

The sequence of reactions in Scheme 1 shows a general approach to the synthesis of compounds of formula 25. In step 1, compound 20 is converted to bicyclic compound 22 through one two pathways, a or b. In step 2, a mono- or di-carbonyl moiety is added, forming compound 23. Compound 23 is then coupled with compound 24.

As shown, compound 22 may be obtained from compound 20 via two pathways. Thus, step 1 of Scheme 1 may proceed through the pathway of step 1(a) or step 1 (b). Depicted below in Sheme 1(a) is step 1(a).

Scheme 1(b) shows the second pathway along which compound 22 may be obtained from compound 20. Particularly, when substituent $R_{75}$ is hydrogen, shown here as compound 20(b), compound 22 may be obtained via reaction with a vinyl magnesium halide.

Scheme 2 depicts addition of a carbonyl group to compound 22, resulting in compound 23(a).

SCHEME 1(a)

Step 1(a)

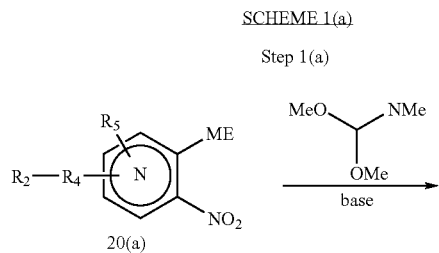

SCHEME 2

Step 2

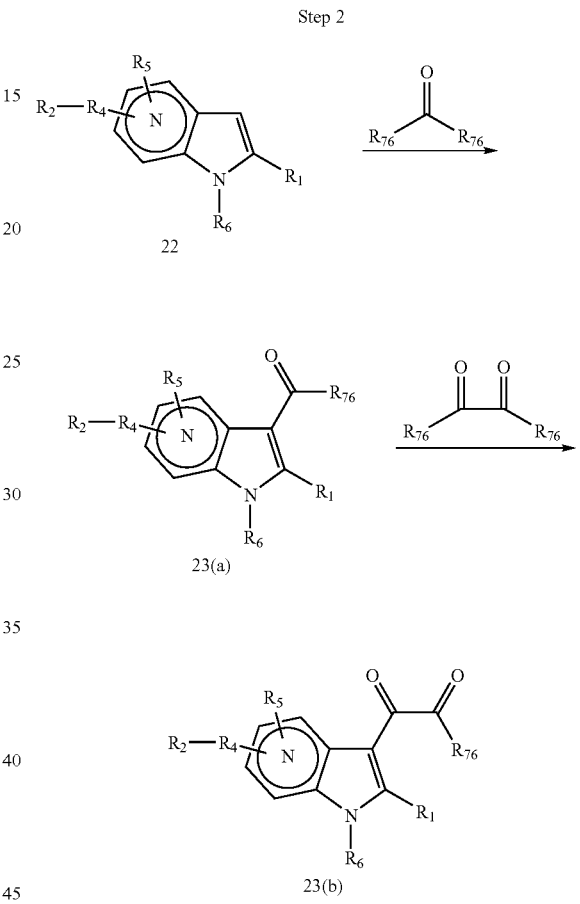

$R_{76}$ is halo and $C_1$ to $C_3$ alkoxy

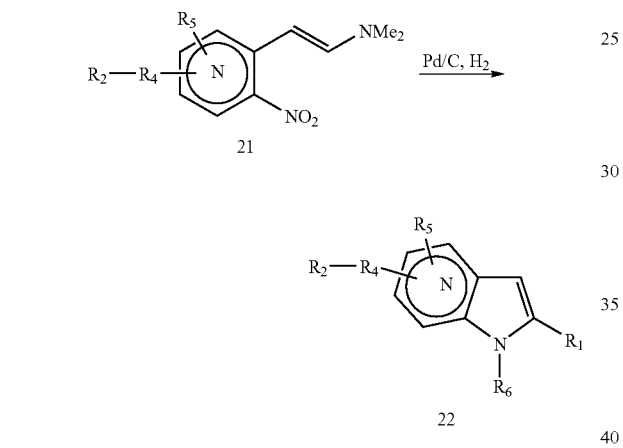

As can be seen, compound 20(a), in which substituent $R_{75}$ is methyl, is reacted under basic conditions with an acetal to form intermediate 21. Enamine 21 is then cyclized to compound 22 via catalytic hydrogenation.

Alternatively, compound 22 may be obtained via the pathway depicted in Scheme 1(b).

Alternatively, a di-carbonyl group may be used, as shown at the bottom of Scheme 2, resulting in di-carbonyl compound 23(b).

Scheme 3 below depicts coupling of compounds 23 and 24.

SCHEME 1(b)

Step 1(b)

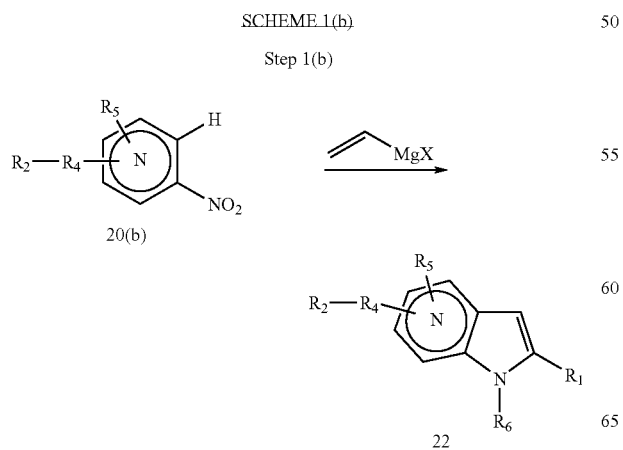

SCHEME 3

Step 3

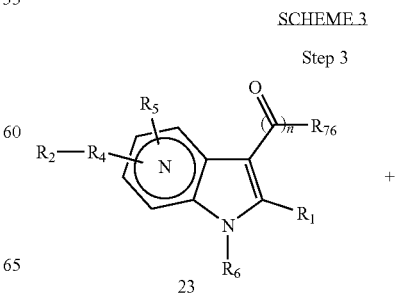

-continued

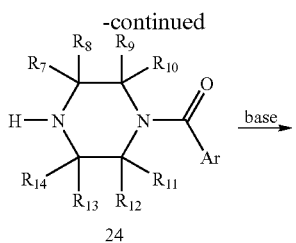
24

Accordingly, one aspect of the present invention relates to a method for preparing compounds of formula 25 through the steps of:

(a)(1) converting a compound of formula 20(a):

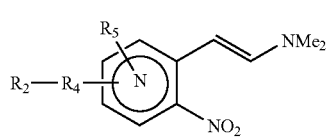
20(a)

to a compound of formula 21:

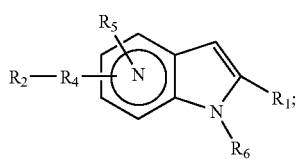
21

(a)(2) converting the compound of formula 21 to a compound of formula 22:

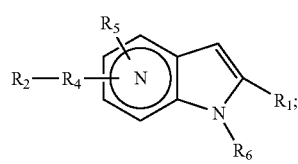
22

(b) converting the compound of formula 22 to a compound of formula 23:

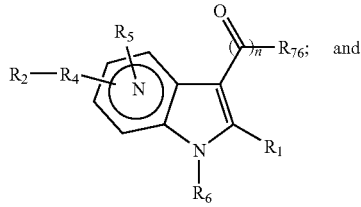
23

(c) coupling the compound of formula 23 with a compound of formula 24:

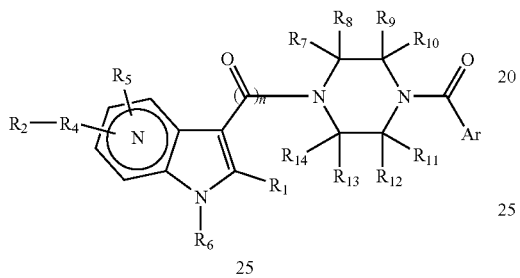
24

More particularly, such a conversion is accomplished through the steps of:

(a) reacting a compound of formula 20(a):

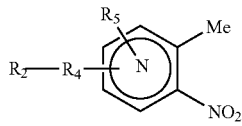
20(a)

in the presence of a base, with

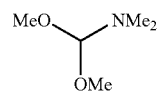

to form a compound of formula 21:

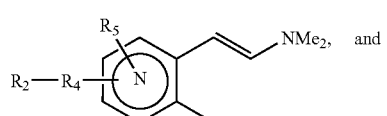
21 catalytically hydrogenating the compound of formula 21 to form a compound of formula 22:

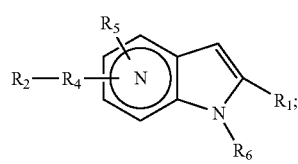
22

(b) reacting the compound of formula 22, in the presence of a Lewis acid, with

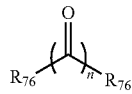

to form a compound of formula 23:

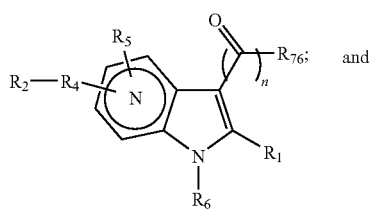

(c) reacting the compound of formula 23, in the presence of a base, with a compound of formula 24:

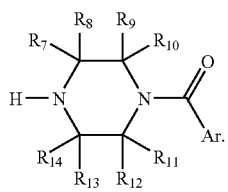

Alternatively, compounds of formula 25 may be prepared via the steps of:

a) converting a compound of formula 20(b):

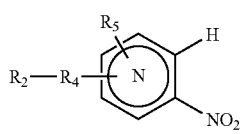

to a compound of formula 22:

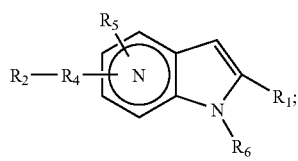

(b) converting the compound of formula 22 to a compound of formula 23:

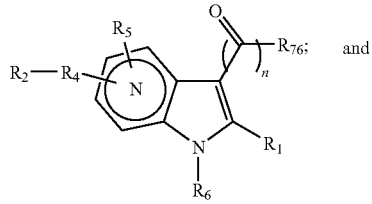

(c) coupling the compound of formula 23 with a compound of formula 24:

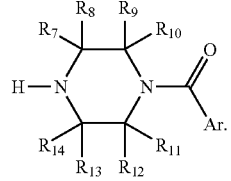

More particularly, the conversion via these steps is accomplished through:

(a) reacting a compound of formula 20(b):

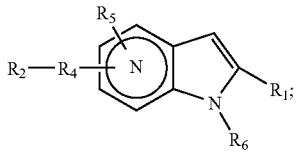

to give a compound of formula 22:

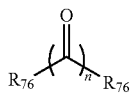

(b) reacting the compound of formula 22, in the presence of a Lewis acid, with to form a compound of formula 23:

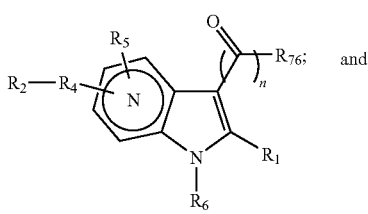

(c) reacting the compound of formula 23, in the presence of a base, with a compound of formula 24:

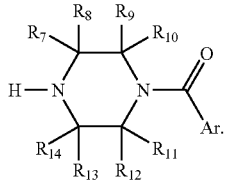

Another aspect of the present invention is shown in detail below in Scheme 2, and in the detailed steps 1-7, which follow.

SCHEME 4

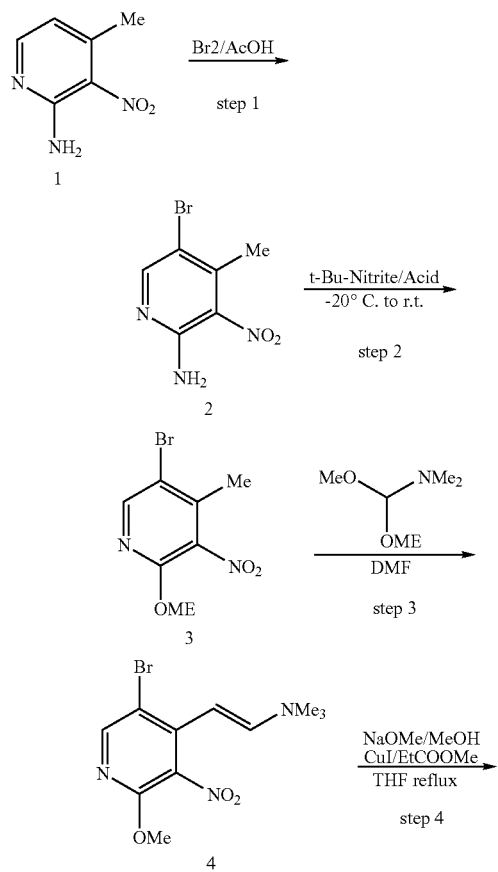

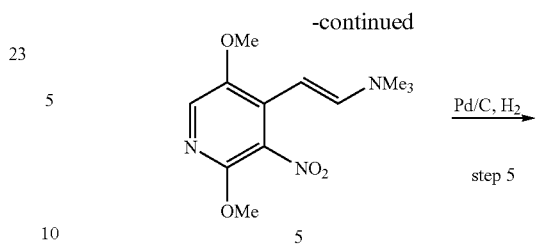

The sequence of reactions in Scheme 4 shows a general organization of the steps from the starting material of compound 1 to the final step resulting in the compound of formula 8. As is shown below, each of the steps may include different reaction conditions to achieve the desired product. This is further shown in the examples, below. Each of the steps are described by corresponding numbers as shown in Scheme 4. Each of the consecutive steps below uses the end product of the previous reaction as the starting material of the next step.

Step 1, the conversion of the compound of formula 1 to the compound of formula 2 is achieved through the introduction of bromine ($Br_2$) in acetic acid (AcOH). The amount of bromine is in the range of about 0.5 to about 2 equivalents (eq.).

Step 2 is conducted with the addition of tert-butyl nitrite (t-Bu-Nitrite) in the presence of an acid. The acid may be generated in situ using acetyl chloride and alcohol. The reaction is exothermic and therefore cooling may be added as necessary. Also, to neutralize acid at the end of the reaction sodium bicarbonate solution may be added.

Step 3 includes the use of N,N-dimethyl formamide-dimethyl acetal in addition to dimethyl formamide (DMF) as a solvent and lithium methoxide (LiOMe) in methanol (MeOH). The reaction is endothermic. Therefore, heat may be added as necessary.

Step 4 is also a slightly exothermic reaction. Copper iodide (CuI) is added in a range of 0.05 to 0.8 eq., desirably from 0.2 to about 0.3 eq. This is followed by the addition of methyl propionate (EtCOOMe) (from about 5 to about 20 eq.), tetrahydrofuran (THF) (from about 5 to about 20 eq.), and sodium methoxide (NaOMe) (from about 5 to about 25 eq.). The reaction mixture is heated to reflux temperature (65° C. to about 75° C.) until the reaction is complete.

Step 5 is the cyclization of the compound of formula 5 to the compound of formula 6 by reduction reaction. A variety of catalysts are useful for this including palladium over carbon (Pd/C), Pd—C transfer hydrogenation conditions, and precious metal catalysts such as Pt/C available as Escat 261 or Escat 160 from Englehard (reductions can also be done using other metals such as Zn, Fe, etc. as well as with sodium dithionate). The reaction is conducted in the presence of ethyl acetate (EtOAc) under hydrogen ($H_2$) pressure in a range from about 10 PSI to about 50 PSI.

Step 6, which represents conversion of the compound of formula 6 to the compound of formula 7, is also includes slightly exothermic reactions which may be controlled by the addition rate. Specifically, after aluminum chloride and the compound of formula 6 is added to a reactor including dichloromethane ($CH_2Cl_2$) in portions, nitromethane ($CH_3NO_2$) is then added followed by methyl chlorooxacetate (ClCO-COOMe) in a range from about 1.0 eq. to about 5.0 eq. The exothermic reaction is controlled by the addition rate of chlorooxacetate. This step may optionally be followed by quenching with a suitable reagent. It has been observed that favorable results were obtained using a preferred embodiment of the process in which first water, and then ammonium acetate are added to quench the reaction mixture.

In Step 7, the compound of formula 7 is coupled with the compound of formula 9 to provide the compound of formula 8. This reaction may, in certain embodiments, be conducted in the presence of sodium tert-butoxide (NaOtBu) in tetrahydrofuran, whereupon improved significantly improved yields, up to about 90% by weight based on total weight of the reaction mixture, may be obtained. HCl may be added after the coupling reaction to neutralize the pH.

The product of step 7, i.e., the compound of formula 8 is then isolated and recrystallized using N-methylpyrrolidone and water. This removes many impurities. A second recrystallization may then be performed to reduce the amount of NMP and achieve a control over the particle size in the final product. This may be performed with a recrystallization solvent including isopropyl alcohol (IPA) and water.

The features and advantages of the present invention are more fully shown by the following examples which are provided for purposes of illustration, and are not to be construed as limiting the invention in any way.

EXAMPLES

Example 1

Step 1

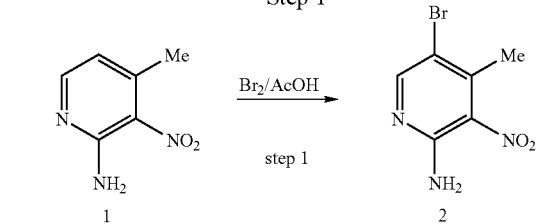

A reaction vessel was purged with inert gas. All steps were performed under inert gas protection.

The vessel was then charged with 7.50 L of acetic acid at 20-25° C. Next, 1.00 kg of the compound of formula 1 was added to the vessel. A yellow suspension was formed. This was followed by the addition of 1.07 kg of sodium acetate. A very thick, yellow suspension was formed and the reaction was noted to be slightly exothermic. The temperature was raised to about 27° C.

The mixture was then cooled to about 15-20° C. and a sample was taken for high pressure liquid chromatography (HPLC) monitoring.

A solution of 1.15 kg of bromine (1.1 eq.) and 2.5 L of acetic acid was prepared. A 10/11 portion of the solution, i.e., 1.0 eq. at 15-20° C. was added to the vessel over about 10-15 minutes. the addition was slightly exothermic and some cooling was necessary ($T_{max}$=20° C.). HPLC was used to monitor the reactions progress immediately after the addition and then at 60 min. Less than 10% of the starting material was observed. Then the remainder of the solution was added and the reaction mixture stirred until completion, approximately 30-60 additional minutes.

After the reaction was complete 10.0 L of ice water was added, dropping the temperature to 10° C. and forming a suspension. The suspension was stirred for another 30-60 minutes and the product was filtered, then washed three times with 2.50 L each time of ice water. The product was dried in at a maximum temperature of 40° C. until reaching constant weight. The yield was 1.45 kg (96.00%) yellow crystals.

Analytical data: m.p. 132° C. IR (KBr, $cm^{-1}$): 1633, 1581, 1538, 1512, 1458, 1377, 1344, 1321, 1244, 869,779. $^1$H-NMR (CDCl$_3$) (δ, ppm): 2.55 (s, 3H), 5.85 (bs, 2H), 8.25 (s, 1H); $^{13}$C-NMR (CDCl$_3$) (δ, ppm): 20.81, 112.14, 144.49, 151.91, 153.78 (2C); MS; (M+1): 232; Elemental Analysis: calcd for $C_6H_6BrN_3O_2$: C, 31.05; H, 2.60; N, 18.11, Br 34.43. found: C, 30.95; H, 2.42; N, 17.45, Br 34.80.

Example 2

Step 2

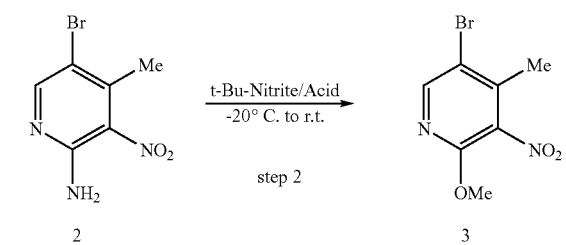

This reaction was conducted under inert gas protection.

The reaction vessel was first charged with 2000 ml methanol and cooled to about 0° C. with slight agitation. Then 9.1 kg acetyl chloride was added. The exothermic reaction was then cooled and agitated for 10 minutes.

The next addition was 100 g 2-amino-5-bromo-3-nitro-4-picoline (the compound of formula 2 at 0° C. Then 236.5 g of t-butyl nitrite was added at a rate such that the temperature did not exceed 5° C. The slight evolution of nitrogen gas was noted. After the completion of the reaction, cooling was removed and the reaction mixture within the vessel was allowed to warm to 25° C. in about 30 minutes.

The mixture was agitated at 25° C. for about 3-4 hours. After 4-5 hours a clear solution was obtained. Reaction completeness was monitored by HPLC after about 4 hours. The reaction was complete after about 5 hours.

The reaction mixture was concentrated in vacuo to about 1000 mL. Then 500 ml of water was added and the product precipitated. Then 250 ml saturated sodium bicarbonate solution was added with good agitation to neutralize the HCl and dissolve the hydroxy impurity. The mixture was agitated at 20-25° C. for about 15 minutes and then the precipitate was collected and washed with 1000 ml of water. The product was then dried at 40° C. in vacuo. Yield was 75.0 g.

Analytical data: m.p. 132° C. IR (KBr, cm$^{-1}$): 1633, 1581, 1538, 1512, 1458, 1377, 1344, 1321, 1244, 869,779. $^1$H-NMR (DMSO-d6) (δ, ppm): 2.31 (s, 3H), 3.96 (s, 3H), 8.55 (s, 1H): $^{13}$C-NMR (DMSO-d6) (δ, ppm): 17.49, 54.91, 99.41, 114.39, 149.23, 153.46; HRMS calcd for C$_7$H$_7$BrN$_2$O$_3$ 245.96401 found (M+1): 246.97184; Elemental Analysis: calcd for C$_7$H$_7$BrN$_2$O$_3$: C, 34.03, H, 2.85, N, 11.34. found: C, 33.81; H, 2.91; N, 11.24.

Example 3

Step 3

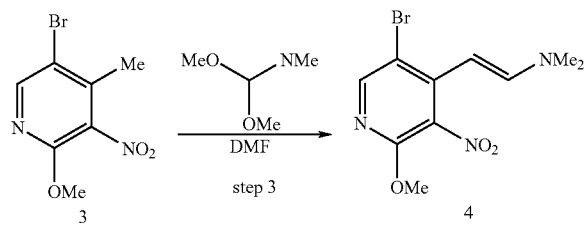

The reaction vessel was purged with inert gas and all steps were performed under inter gas protection.

The vessel was charged with 100 g of the compound of formula 3. Then 800 mL of dimethyl formamide (DMF) was added followed by 39.5 mL of 1.0 M solution of LiOMe in MeOH (32.25 g, 0.0395 mmol). The reaction was heated to 80° C.

The next addition to the vessel was 430.17 mL N,N-dimethyl formamide-dimethyl acetal (3.23 mmol, 8 eq.) over 10 minutes. An endothermic reaction was noted. The reaction was heated to 95° C. and completed in about 8-10 hours as confirmed by HPLC. After the reaction was complete, it was cooled to room temperature. 1200 mL water was added, while maintaining the temperature of the reaction mixture above about 40° C.

A red solid precipitated which was filtered and then washed with two 300 mL portions of water. The product was dried to obtain the compound of formula 4. Karl Fischer (KF) titration revealed the water content to be about 0.08-0.11%.

Analytical data: m.p. 132° C. IR (KBr, cm$^{-1}$): 1629, 1582, 1487, 1407, 1309, 1081. $^1$H-NMR (CDCl$_3$) (δ, ppm): 2.92 (s, 6H), 3.94 (s, 3H), 4.92 (d, 1H), 7.0 (d, 1H), 8.15 (s, 1H): $^{13}$C-NMR (CDCl$_3$) (δ, ppm): 54.79, 87.94, 112.08, 140.15, 147.59, 148.57, 155.03; MS calcd for C$_{10}$H$_{12}$BrN$_3$O$_3$ 301.01 found (M+1): 302.0.

Example 4

Step 4

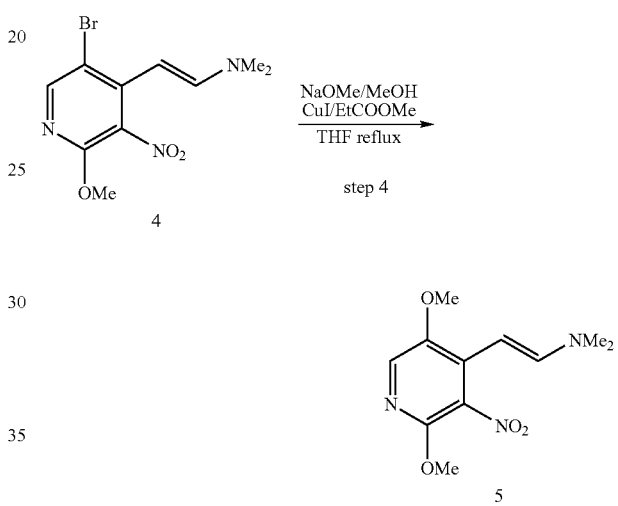

The reaction vessel was purged with inert gas and then charged with 250 g (0.827) of the compound of formula 4, then 31.52 g CuI (0.165 mol, 0.2 eq.), 875 mL methyl propionate (about 9.102 mol, 11 eq.), 875 mL tetrahydrofuran (about 10.787 mol, 13 eq.), and 2838 mL NaOMe (25% in MeOH)(12.412 mol, 15 eq.). Exothermic reaction was noted, 21° C. to about 27° C. The reaction was heated to reflux temperature (about 69-71° C.) until the reaction was complete (about 20 hours).

The reaction mixture was cooled to around 5° C. Then the vessel was charged with 4960 mL of 3.7 M NH$_4$Cl (aq.)(about 3.5-3.9M). Exothermic reaction was noted (about 26° C. to about 29° C.) and pH changed from about 13.0-13.5 to about 9.2-9.7.

The reaction mixture was filtered to collect the precipitate. The product was then washed until the washings were free of halide (AgNO$_3$ test negative). The product was then dried under vacuum oven at 50° C. until KF<0.1% obtaining 165.3 g of the compound of formula 5.

Analytical data: m.p. 167~168° C. IR (KBr, cm$^{-1}$): 1629, 1582, 1487, 1408, 1309, 1081. $^1$H-NMR (DMSO-d$_6$) (δ, ppm): 2.87 (s, 6H), 3.82 (s, 3H), 3.89 (s, 3H), 4.51 (d, 1.2 Hz, 1H), 7.74 (s, 1H), 7.83 (d, 1.5 Hz, 1H). $^{13}$C-NMR (DMSO-d$_6$) (δ, ppm): 53.6, 56.8, 82.2, 128.6, 130.2, 131.2, 146.6, 148.9, 150.3. HR-MS: calcd for C$_{11}$H$_{16}$N$_3$O$_4$ (M+H$^+$): 254.1141.

found: 254.1138. Elemental Analysis: calcd for $C_{11}H_{15}N_3O_4$: C, 52.16; H, 5.97; N, 16.59. found: C, 51.91; H, 5.73; N, 16.43.

Example 5

Step 5

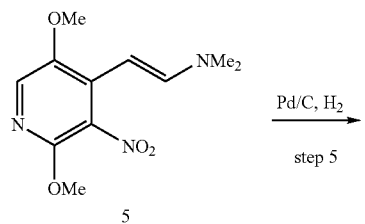

The compound of formula 5 (15 g) was charged into a 1L glass buchii hydrogenation reactor followed by 1.5 g of Escat-261 (1% Pt/C, ~59% wet), 300 mL of ethyl acetate, and the reactor was purged three times with nitrogen (25 PSI each). The first purge was without stirring, followed by second and third with 100-200 rpm stirring. Then the reactor was purged three times, while stirring with hydrogen gas and the reactor was pressurized at 25 PSI with hydrogen at 25° C. internal temperature.

The reaction RPM was set to 800 and the hydrogen uptake was followed. The reaction was stopped with the hydrogen uptake stabilized. An aliquot was diluted at 100× and tested by HPLC to test completion as well as product to impurity ratio.

The catalyst was filtered off and the filtrate washed with 10 mL ethyl acetate. Then to the filtrate was added 150 mL of deionized water (DI water) and stirred for 20 minutes. Then 7.11 mL of acetic acid was added and stirred for 30 minutes. The mixture was allowed to separate and the slightly pinkish aqueous layer was removed. Two more additions of 150 mL of DI water were introduced to the organic layer and stirred for 30 minutes followed by separating and removing the aqueous layer.

The last two removed aqueous layers were combined and stirred with 50 mL ethyl acetate for 20 minutes. The organic layer was removed and combined with the original organic layer. The total organic layer was transferred to a 1L 3-necked flask with mechanical stirrer. 16 mL isopropanol (IPA) was added followed by 7.7 mL of TMSCl added dropwise at room temperature over a ten minute period. The resulting slurry was stirred for one hour at room temperature then filtered and the filtrate washed with two 20 mL portions of ethyl acetate. The cake was dried at 40° C. in a vacuum oven for 15 hours. The yield was white solid 11.09 g.

Analytical data: m.p. 294.81° C. IR (KBr, cm$^{-1}$): 1629, 1582, 1487, 1408, 1309, 1081. $^1$H-NMR (DMSO-d$_6$) (δ, ppm): 3.90 (s, 3H), 4.20 (s, 3H), 6.58 (bs, 1H), 7.12 (s, 1H), 7.74 (bs, 1H). $^{13}$C-NMR (DMSO-d$_6$) (δ, ppm): 56.41, 58.06, 100.83, 107.13, 107.17, 119.84, 128.61, 132.20, 145.61, 145.75. MS: calcd for $C_9H_{10}N_2O_2$: 178.07. found: 179 (M+1).

Example 6

Step 6

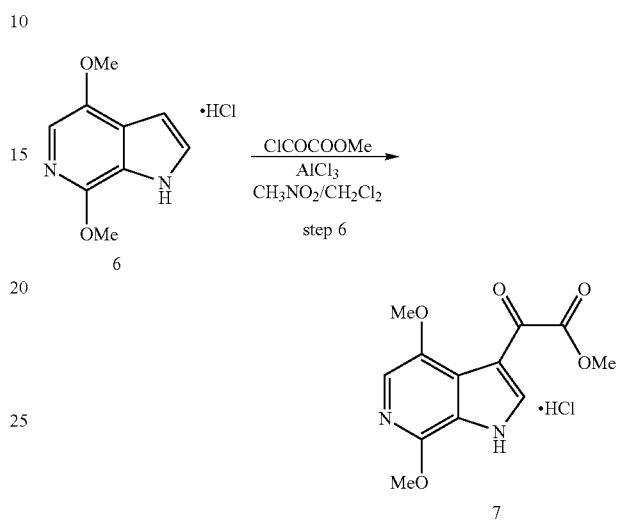

The reaction was conducted under nitrogen blanket. A reactor was charged with 27.7 g AlCl$_3$ (4.4 eq.) followed by 180 mL dichloromethane with argon protection. The reaction mixture was cooled to about −20° C. with agitation. Then the compound of formula 6 (HCl-salt) (10.00 g) was added in portions, rinsed with 20 mL dichloromethane and stirred for 15 minutes. A slight exothermic reaction was noted and the temperature range was controlled in a range from about −15° C. to about −20° C.

The next addition was 34.0 mL nitromethane, added dropwise, then rinsed with 10 mL dichloromethane, while maintaining the temperature from about −15° C. to about 20° C. controlled by the addition rate. The mixture was agitated for 5 minutes.

Fifteen (15.0) mL of methyl chlorooxoacetate was then added at a rate such that the temperature did not exceed −15° C. and rinsed with 10 mL dichloromethane. After the addition, the mixture was agitated at −20° for 30 minutes and a sample was taken for HPLC.

A solution was prepared including 50 g ammonium acetate in 200 mL water and 50 mL of dichloromethane. The solution was cooled to about 0 to about −5° C. The solution was then combined with the reaction mixture keeping the temperature below about 15° C.

The reactor was rinsed with a mixture of 20 mL CH$_2$Cl$_2$ and 20 mL water. The product is in the lower organic phase. The upper aqueous phase was extracted with 50 mL dichloromethane and the organic phases were combined. The organic phase was then treated with vacuum to speed the distillation off of the dichloromethane, reducing the volume to about 80-100 mL. Under the continuous vacuum, 240 mL of isopropyl alcohol was added, then distilled to a final volume of 8 mL/g. After the distillation, the reaction mixture is brought to about 50° C.

A separate (second) reactor was charged with 30 mL isopropanol and cooled to 0° C. Then, 3 mL acetyl chloride was added and agitated for 30 minutes. An exotherm of 10-12° C. was observed.

To the solution in the first reactor, 10 mL of the solution in the second reactor was added dropwise over 5 minutes to induce crystallization. The mixture was held at 50° C. for 20 minutes, then the remaining solution from the second reactor was added.

Following the reaction, the mixture was cooled to room temperature and agitated for one hour. Then the mixture was cooled to 0-5° C. and agitated for about one hour. The precipitate was collected and washed with 70 mL IPA. The compound was dried until the loss on drying (LOD) was less than about 0.3%. The yield was about 75-80%.

Analytical data: mp 147.4-149.6° C. (dec); $^1$H NMR: (DMSO-d6, ppm) δ 13.26 (br s, 1H), 9.07-9.50 (br, 1H), 8.28 (d, J=3.3 Hz, 1H), 7.45 (s, 1H), 4.02 (s, 3H), 3.84 (s, 3H), 3.83 (s, 3H); $^{13}$C NMR: (DMSO-d6, ppm) δ 181.50, 164.87, 146.35, 145.72, 137.55, 123.85, 121.91, 115.68, 113.91, 56.94, 55.42, 52.56;

Elemental analysis: Calc: C, 47.93; H, 4.36; N, 9.32, Cl, 11.79. Found: C, 47.66, H, 4.58, N, 9.20, Cl, 11.66.

Example 7

Step 7 Including Isolation and Recrystallization

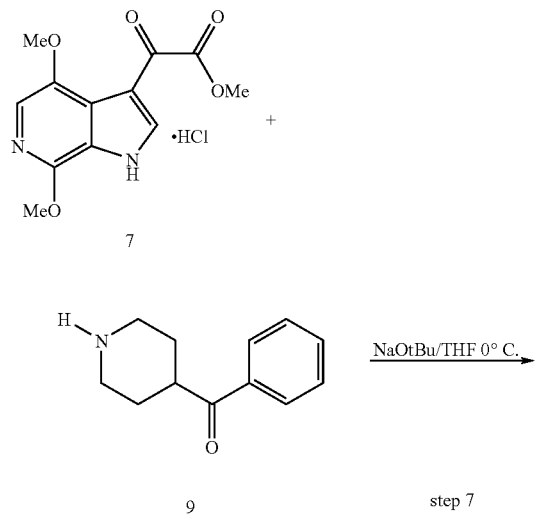

step 7

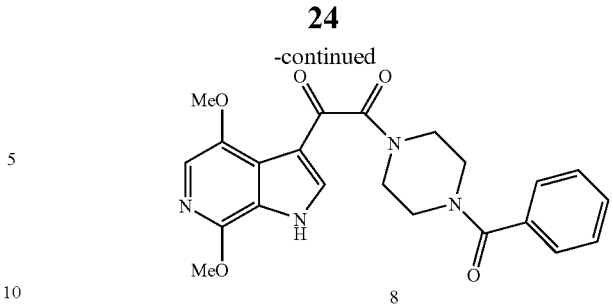

8

Into a 300 mL mini-reactor was charged 12.0 g of the compound of formula 7 and 9.95 g of the compound of formula 9, followed by 137 mL of THF. The mixture was stirred to give a slurry, then cooled to −5 to 5° C. with stirring. Then 59.1 mL 30 wt % NaOtBu was added to the slurry keeping the temperature below 10° C.

HPLC was monitored for completion of the reaction which was complete in about 2.5 hours. The reaction mixture was then transferred by vacuum to 72 mL water in a 500 mL mini reactor. The mixture was stirred for 30 minutes to hydrolyze the residual starting material.

Then 72 mL of 1N HCl was added over 2 minutes (pH 9.23). The HCl was added in 1 mL portions to pH 6.75 (a total of 86 mL 1N HCl). The mixture was biphasic solution before and after neutralization.

130 mL of THF was evaporated and solids started to precipitate; temp of pot 68° C., vapor 64° C., jacket set at 80° C.). NMP (72 mL) was then added. The solids did not all dissolve but darker colored material on the walls of the reactor dissolved (presumably impurities). The evaporation was continued until 192 mL of distillate had been collected and distillation was much slower; calculated volume of distillate expected 207 mL. Final temperatures were: jacket 105° C., pot 89° C., vapor 79° C.

The mixture was cooled to room temp over one hour and stirred at room temperature for 18 hours. Then the mixture was cooled to 0-5° C. over one hour and stirred at 0° C. for two hours. The product was collected and rinsed with 4×24 water and then dried.

Analytical data: mp 243-245° C.; $^1$H NMR: (DMSO-d6, ppm) δ12.98 (s, 1H), 8.14 (d, J=2.5 Hz, 1H), 7.47 (bs, 6H), 3.99 (s, 3H), 3.84 (s, 3H), 3.64 (bs, 4H), 3.38 (bs, 4H); $^{13}$C NMR: (DMSO-d6, ppm) δ 186.32, 170.01, 167.26, 146.96, 146.54, 137.29, 136.26, 130.38, 129.13, 127.74, 123.05, 122.90, 120.12, 115.21, 57.66, 53.63, 45.89, 41.27; Elemental analysis: Calc: C, 62.55; H, 5.24; N, 13.26. Found: C, 62.28, H, 5.14, N, 13.17.

Example 8

Isolation and Recrystallization of Formula 8

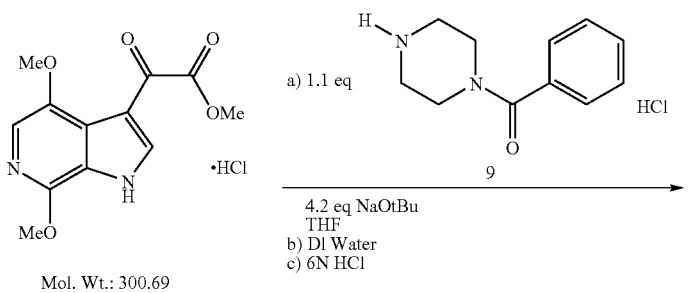

a) 1.1 eq 4.2 eq NaOtBu
THF
b) DI Water
c) 6N HCl

Mol. Wt.: 300.69

-continued

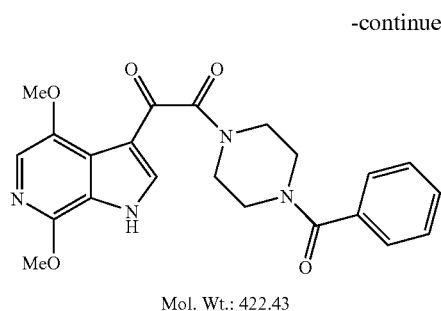

Mol. Wt.: 422.43

+ 4.2 eq. t-BuOH
+ 4.2 eq. NaCl
+ 1 eq. MeOH

+0.1 eq.

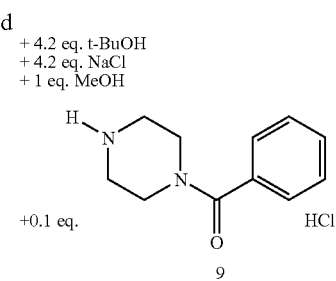

9

Balanced Side Reaction

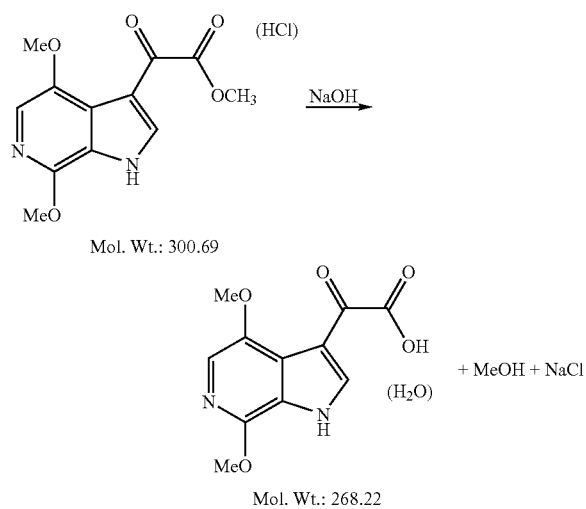

The pH was adjusted with 6N HCl to achieve a pH of about 6.5.

Then the reaction mixture was heated from 6.6° C. to 61.5° C. over 70 minutes to begin the distillation. The level in the reactor was maintained by charging NMP. The distillation temperature reached a maximum at the end of the distillation at 89.8° C. The batch was then assayed by GC to find 1.85% THF, 1.42% t-BuOH and 31.55% NMP by volume.

Water was then charged which was pre heated to 70.1° C., then transferred to the reaction mixture over 18 min. The batch temperature was maintained at 77° C. through the transfer. The batch was then held for 37 minutes at 74.6° C. to 77° C. Cooling was initiated slowly, bringing the slurry from 74.6° C. to 10.0° C. over 3 hours and 9 minutes. It was then held for 62 minutes from 6.3° C. to 10.0° C. A filtered sample showed the mother liquor to have 5.23 mg/ml of formula 8 and 3.88 mg/ml of formula 9.

Isolation:

The product was isolated on centrifuge. The composite KF of the wet cake was 4.97%.

Drying:

The cake was dried in the tray dryer. Heat and vacuum were applied averaging 35.6° C. and 22.8 mmHg, respectively. After 12 hours, product was dry and had representative moisture contents ranging from 1.74% to 2.15% KF.

Recrystallization:

In a reactor 18.56 kg of the compound of formula 8 was charged, followed by 280.4 kg IPA/water recrystallization solvent, charged over 23 minutes. The reactor was heated from 28.8° C. to 78.8° C. over 2 hours 28 minutes and stirred in the 78.8 to 80.2° C. temperature range for 21 minutes. An additional 23.7 kg recrystallization solvent rinse was charged, and the mixture held for 5 hours 11 minutes between 78.8 and 81.4° C. The seed slurry was prepared by charging 0.191 kg of the compound of formula 8 to a carboy, followed by 1.5 kg Isopropanol. Reactor was heated to 60° C., and the batch transferred over 30 minutes through polish filter F57 into Reactor. The batch temperature was 67.9° C. after the transfer. The batch was cooled from 68.2° C. to 42.3° C. over 62 minutes. The slurry of seeds was added over 2 minutes and the batch cooled to 20° C. over 36 minutes. The batch was held for 15 hours 45 minutes at ambient temperature.

Isolation/Drying:

The 363 L slurry was filtered over 13 minutes using Robatel 540 mm centrifuge C-9 with a loading speed of 900 rpm and a deliquoring speed of 900 rpm using a 5-10 μm polypropylene bag. The material was washed with 27.5 kg IPA and deliquored for 1 hour 36 minutes. The cake thickness in C9 was 6.2 cm for the 16.2 kg of wet cake isolated. The LOD's of the wet cake at top, middle and bottom were 3.79, 3.71 and 5.10% respectively.

Drying:

The cake was dried in the 316SS tray dryer D6 with 16.20 kg over 4 trays. Heat and vacuum were applied averaging 45° C. and 21 mmHg, respectively. After 19 hours, the 15.37 kg of product was dry having representative LODs ranging from 0.47% to 0.60%.

Delumping/Blending:

15.22 kg dry compound of formula 8 was milled at approximately 200 rpm using M1(Quadro Comil fitted with round-end impeller) with screen size 0.055" over 45 minutes. The material was then blended in a 30-gal container for 35 minutes in GR-8 at 50 rpm to give 15.10 kg output of delumped and blended product.

The azaindole compounds prepared according to this invention have demonstrated utility as antiviral agents that inhibit the HIV virus, alone, or in combination with other pharmaceutical agents and/or excipients. Azaindole oxoacetic piperazine amides, and their usefulness as HIV inhibitors, have been disclosed in two series of patent applications. The first series discloses azaindole derivatives which have promising potential as antiviral agents, Wang, Tao et al., U.S. Pat. No. 6,476,034 and PCT Application WO 0162255 A1, filed Jan. 19, 2001, published Aug. 30, 2001. The second series, Wang, Tao, et al. discloses HIV Antiviral Activity of Substituted Azaindoleoxoacetic piperazine Derivatives in U.S. patent application Ser. No. 10/214,982 filed Aug. 7, 2002, which is a continuation-in-part application of U.S. Ser. No. 10/038,306 filed Jan. 2, 2002 (corresponding to PCT Appl. (PCT/US02/00455), WO 02/062423 A1, filed Jan. 2, 2002, published Aug. 15, 2002. The subject matter of all the above-mentioned applications is incorporated by reference herein.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A method of preparing a compound of formula 8:

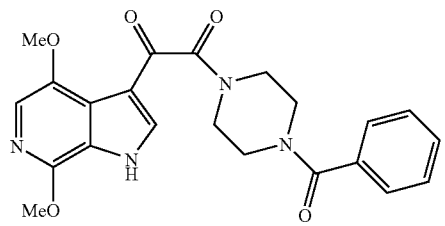

comprising the steps of:

(a) converting a compound of formula 1:

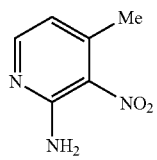

to a compound of formula 2:

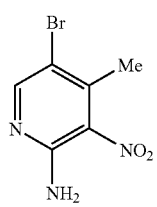

(b) converting said compound of formula 2 to a compound of formula 3:

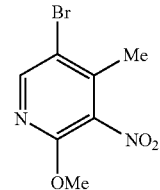

(c) converting said compound of formula 3 to a compound of formula 4:

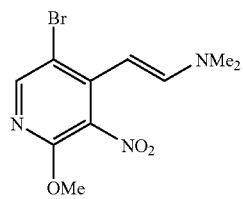

(d) converting said compound of formula 4 to a compound of formula 5:

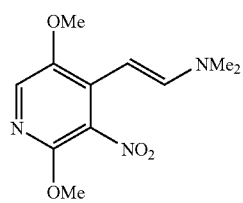

(e) cyclizing said compound of formula 5 to a compound of formula 6:

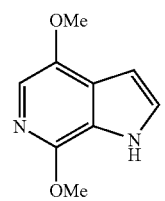

(f) converting said compound of formula 6 to a compound of formula 7:

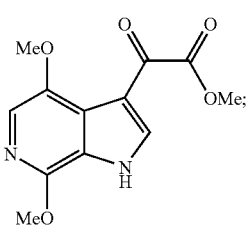

and (g) coupling said compound of formula 7 with a compound of formula 9:

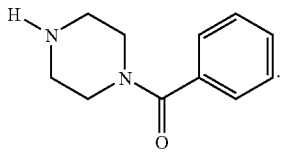

2. The method of claim 1, wherein said converting said compound of formula 1 to said compound of formula 2 is conducted with the addition of bromine and acetic acid.

3. The method of claim 1, wherein said converting said compound of formula 2 to said compound of formula 3 is conducted with tert-butyl nitrite in the presence of acid.

4. The method of claim 1, wherein said converting said compound of formula 3 to said compound of formula 4 is conducted with N,N-dimethyl formamide-dimethyl acetal in the presence of lithium methoxide in methanol and dimethyl formamide.

5. The method of claim 1, wherein said converting said compound of formula 4 to said compound of formula 5 is conducted in the presence of copper iodide, methyl propionate, tetrahydrofuran, and sodium methoxide.

6. The method of claim 1, wherein said cyclizing said compound of formula 5 to said compound of formula 6 is conducted with a precious metal catalyst in the presence of ethyl acetate or Pd/C or catalytic transfer hydrogenation or reduction with sodium dithionate.

7. The method of claim 6, wherein said precious metal catalyst comprises Pt/C.

8. The method of claim 1, wherein said converting said compound of formula 6 to said compound of formula 7 is conducted with aluminum chloride followed by the addition of chloromethane, nitromethane, and chlorooxoacetate.

9. The method of claim 1, wherein following step (f), the reaction is quenched with water, and then with ammonium acetate.

10. The method of claim 1, wherein said coupling the compound of formula 7 with the compound of formula 9 is conducted in the presence of sodium tert-butoxide and tetrahydrofuran.

11. A method of preparing a compound of formula 8:

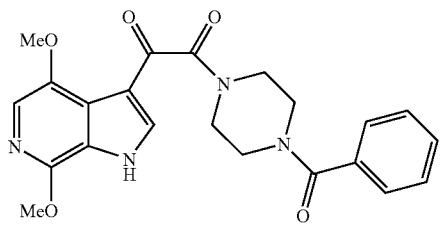

comprising the step of coupling a compound of formula 7:

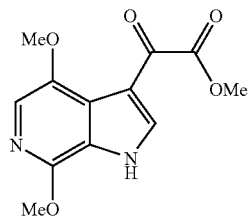

with a compound of formula 9:

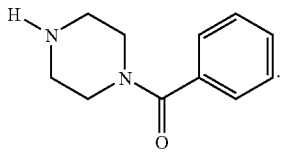

and wherein the yield of the compound of formula 8 is up to about 90% weight, based on total weight of the reaction mixture;

and further wherein said compound of formula 7 is prepared by the steps of:

(a) cyclizing a compound of formula 5:

to a compound of formula 6:

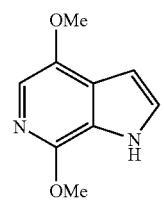

(b) converting said compound of formula 6 to said compound of formula 7.

12. The method of claim 11, wherein said compound of formula 5 is prepared by the step of converting a compound of formula 4:

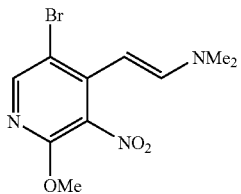
4 to said compound of formula 5.

13. The method of claim 12, wherein said compound of formula 4 is provided by:

(a) converting a compound of formula 2:

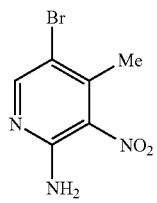
2 to a compound of formula 3:

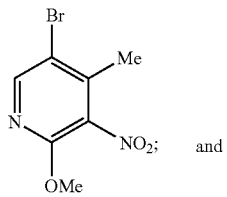
3 and (b) converting said compound of formula 3 to said compound of formula 4.

14. A method of isolating the compound of formula 8 as prepared in claim 1 comprising the steps of:

(a) distilling the product of step (g) in a reactor while charging with N-methylpyrrolidone to maintain volume;
(b) charging said reactor with water; and
(c) isolating said product on centrifuge.

15. The method of claim 14 further comprising the step of recrystallizing said product with a mixture comprising isopropyl alcohol and water.

* * * * *